(12) United States Patent
Jung et al.

(10) Patent No.: US 7,311,671 B2
(45) Date of Patent: Dec. 25, 2007

(54) DEVICE FOR SAMPLE COLLECTION AND STORAGE

(75) Inventors: Jaean Jung, Monroe Township, NJ (US); Young Ho Choi, Princeton, NJ (US)

(73) Assignee: Access Bio, Inc., Monmouth Jct., NJ (US)

( * ) Notice: Subject to any disclaimer, the term of this patent is extended or adjusted under 35 U.S.C. 154(b) by 146 days.

(21) Appl. No.: 10/724,474

(22) Filed: Nov. 28, 2003

(65) Prior Publication Data

US 2004/0116826 A1    Jun. 17, 2004

Related U.S. Application Data

(60) Provisional application No. 60/429,972, filed on Nov. 29, 2002.

(51) Int. Cl.
*A61B 10/00* (2006.01)
*A61B 5/00* (2006.01)
*B65D 81/00* (2006.01)

(52) U.S. Cl. .................. 600/562; 600/572; 600/573

(58) Field of Classification Search ............ 600/562, 600/569, 570, 571, 578, 583, 584, 572, 573, 600/576; 604/1

See application file for complete search history.

(56) References Cited

U.S. PATENT DOCUMENTS

| | | | | | |
|---|---|---|---|---|---|
| 4,353,868 | A | * | 10/1982 | Joslin et al. | 422/101 |
| 4,370,987 | A | * | 2/1983 | Bazell et al. | 600/573 |
| 4,883,068 | A | * | 11/1989 | Dechow | 600/573 |
| 5,275,953 | A | * | 1/1994 | Bull | 436/69 |
| 5,308,580 | A | * | 5/1994 | Clark | 422/58 |
| 5,766,962 | A | * | 6/1998 | Childs et al. | 436/518 |
| 5,980,828 | A | * | 11/1999 | McClintock et al. | 422/58 |
| 6,602,205 | B1 | * | 8/2003 | Erickson et al. | 600/573 |

OTHER PUBLICATIONS www.copanusa.com/html/aero_liq.html.*

* cited by examiner

*Primary Examiner*—Max F. Hindenburg
*Assistant Examiner*—Jonathan Foreman
(74) *Attorney, Agent, or Firm*—Joseph Hyosuk Kim; JHK Law

(57) ABSTRACT

The present application describes a device for collecting biological samples comprising at least one collection protrusion comprising at least one tip; and at least one pad for contacting the tip.

20 Claims, 4 Drawing Sheets

DEVICE FOR SAMPLE COLLECTION AND STORAGE

This nonprovisional application claims priority under 35 U.S.C. § 119(e) on U.S. Provisional Application No. 60/429,972 filed on Nov. 29, 2002, which is herein incorporated by reference.

BACKGROUND OF THE INVENTION

1. Field of the Invention

The present invention relates to a device for collecting and storing biological specimen for storage with decreased level of degradation of the degradable material within the sample.

2. General Background and State of the Art

Cells in a biological sample contain nucleic acids, proteins, carbohydrates, lipids and so on. At least in the case of DNA, it is possible to identify with great accuracy the identity of the source organism of the biological specimen, so long as the DNA is left fairly in tact so as to be analyzable. In one type of situation, DNA fingerprinting is currently used to identify individuals using hair samples from the crime scene, which are analyzed for DNA content and matched with suspect's reference DNA. And there are many other valuable uses for DNA analysis, such as to determine paternity and family lineage.

Since all organisms, including microorganisms, bacteria, fungi, plants, viruses, and other living organisms contain genetic material, another valuable use for DNA analysis is in determining the identity of certain non-human organisms. However, left in its natural state, the particular cells and the genetic material may degrade and not leave enough time for the DNA analyst to study the genetic material before the genetic material has lost its integrity.

It is also desirable to collect and store non-genetic biological molecules, such as carbohydrates, lipids, and proteins, including but not limited to toxins, polypeptides, endotoxins, exotoxins and so on.

Given the advantages and desirability of analyzing DNA from a biological specimen, as well as other methods of analysis, such as high pressure liquid chromatography (HPLC) to detect the presence of various biological molecules, which do not necessarily include genetic material, there is a need to collect these samples and store them for long periods of time. Therefore, there is a need in the art to provide an apparatus for collecting the biological specimen and storing them for a long time with minimal degradation so that the biological material is substantially intact to be analyzed.

SUMMARY OF THE INVENTION

The invention provides solutions to the above-mentioned problems.

Advantages of the invention include the capability of easily collecting various types of samples, such as cells in liquid solution or solid materials, whole blood, epithelial cells, bone, hair, skin, nail and so on.

An especially advantageous feature for use by the military is that a field soldier can collect various samples from any environmental condition. In certain respects, the invention is directed to a sample collection and storage kit that may be used to collect and store biological samples in the battlefield or in biological warfare. Individual soldiers may use this kit to collect samples from suspected surface area in either or both solid and liquid form. Such collected sample may include microorganisms, toxins, chemicals, and any other material, which may be further analyzed. Accordingly, the inventive device may be used to gather biological samples to detect and identify biological molecules in combating bioterrorism.

Other advantages include the longevity of storage up to 1 to 10 years depending on storage condition. Under certain conditions, samples can be stored for longer than 10 years and remain viable for testing, in particular, DNA testing.

The inventive sample collection kit may store epithelial tissue, hair, blood, nail, teeth and so on for DNA analysis and/or archiving purposes. For instance, samples can be collected from family members or school children to archive their genetic information. These samples can be used to make reference data, which can be compared with other samples to determine whether there is a match between the reference and the sample.

In one aspect, the present invention is directed to a device for collecting biological samples comprising:
  (i) at least one collection protrusion comprising at least one tip; and
  (ii) at least one pad for contacting the tip.

The tip may be made of any material, which is suitable for gathering a biological sample, such as a wick, spoon, pick, or swab. Further, the pad may comprise chemical preservatives or enzyme inhibitors. The device may comprise at least one cap, which sealingly encloses the device. In one aspect, the cap may be connected to the device. The cap may be detached from the device. And further, the cap may slidably enclose the device.

In one aspect of the invention, the device may be made from any material at all, so long as the device is suitable for gathering biological samples. In one aspect, the device may be made of plastic. Further, the sample may comprise nucleic acid.

The invention is further directed to instructions that describe a method of collecting biological samples using the device described above. The instructions may be in written form, such as but not limited to a label on device or a sample collection manual. Such a device may be a suitable for collecting any biological or environmental sample. The instructions may be via a computer screen via cathode ray tube, LCD, LED, and so on, so long as the instructions are visible through the eye. The instructions may also be in the form of audio/visual media.

In the device described above, at least one collection protrusion may be foldable or removable.

In another aspect of the invention, the device for collecting biological samples comprises:
  (i) at least one collection protrusion comprising at least one tip;
  (ii) at least one pad for contacting the tip; and
  (iii) a storage area for collecting liquid and/or solid sample.

In another aspect of the invention, the inside of the liquid storage area may contain chemical preservative or enzyme inhibitor, such as by coating the wall of the area. Further, the liquid storage area may be fitted with a syringe. In one aspect, the syringe may be fitted with a unidirectional piston. In another aspect, the liquid storage area may be fitted with tubing. Further, the tubing may be capillary tube.

In still another aspect, the device may further include an area for gathering a solid sample. The solid sample collection area may comprise a lid.

These and other aspects of the invention will be more fully understood from the following description of the invention, the referenced drawings attached hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein;

In FIG. 1A, the device is open. In FIG. 1B, the device is closed.

DETAILED DESCRIPTION OF THE PREFERRED EMBODIMENTS

In the present application, "a" and "an" are used to refer to both single and a plurality of objects.

As used herein, "sample" or "biological sample" is referred to in its broadest sense, and includes solid and liquid or any biological sample obtained from nature, including an individual, body fluid, cell line, tissue culture, or any other source, which may contain genetic material. As indicated, biological samples include body fluids, such as blood, semen, lymph, sera, plasma, urine, synovial fluid, spinal fluid, sputum, pus, sweat, as well as liquid samples from the environment such as plant extracts, pond water and so on. Solid samples may include animal or plant body parts, including but not limited to hair, fingernail, leaves and so on.

The Device

Figure 1A:
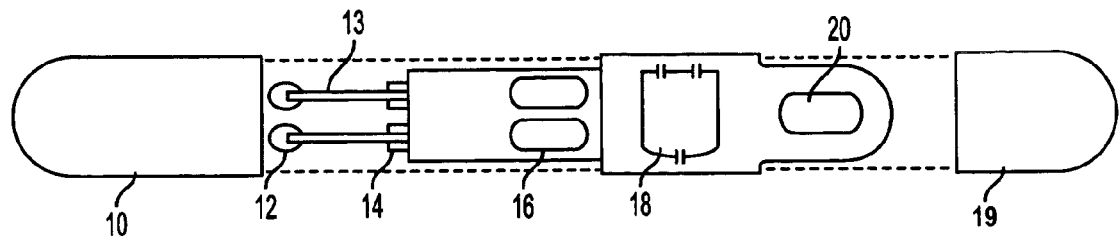
FIGS. 1A-1B show top view of the device fully opened.
Figure 1B:
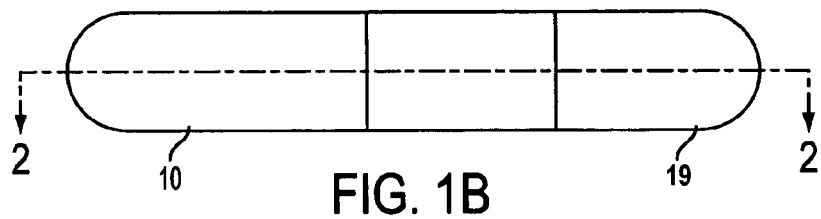
Figure 2:
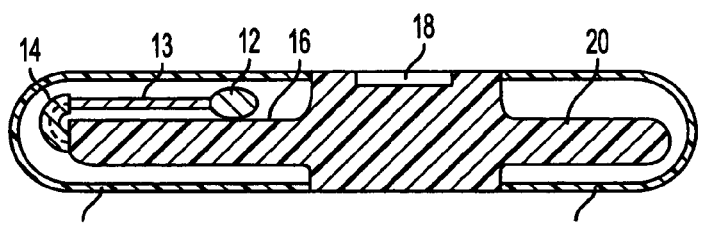
FIG. 2 shows side view of the device closed.
Figure 8:
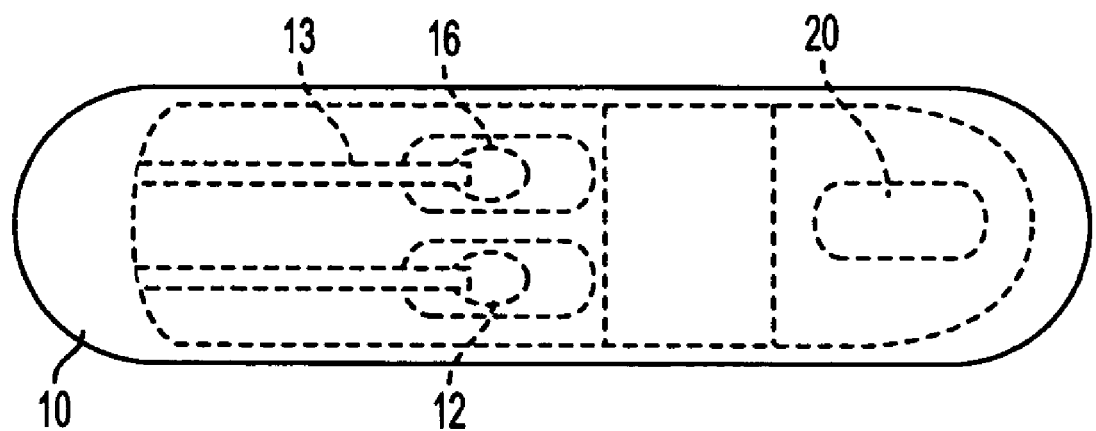
FIG. 8 shows the device fully closed with alternative embodiment of the cap.

The inventive device comprises a plurality of areas for collecting and storing biological samples. As seen in FIGS. 1A-1B, 2 and 8, there is a space or chamber for liquid specimen storage (20); a space or chamber for depositing solid specimen (18); a space, chamber or pad (16) for depositing biological sample obtained by use of a sample collection protrusion; and a sample collection protrusion (13) with a collection structure at the tip (12). The collecting areas may be covered by caps (10, 19). FIGS. 1A-1B show open (FIG. 1A) and closed (FIG. 1B) views of the device. FIG. 2 shows a side view of the device in which the caps (10, 19) cover the area that the sample gathered through the protrusion (16) is deposited, and the liquid sample collection area (20). FIG. 8 shows top view of an alternative embodiment of the device in which the caps cover substantially all of the device.

It is to be noted that each collecting area may be placed as a stand alone or the collecting areas may be placed in any combination, in any order. For example, the sample collection protrusion may be placed between the liquid specimen storage chamber and the solid specimen storage chamber. It is also to be recognized that the inventive device may include other collection and storage spaces in addition to the ones mentioned herein.

In still another aspect of the invention, the inventive sample collection device comprises a plurality of aeration holes in any of the chambers to help dry the samples and reduce humidity within the chamber, including chambers in which padding is used to deposit samples.

In one embodiment, the caps slidingly and sealingly cover the collecting areas. In particular, the cap (10, 19) covers the whole blood collection area or biological liquid specimens which contain nucleic acid moleculues such as DNA or virus and the like. The cap and may be coated with silica gel or a molecular sieve, and may be further coated with a desiccant, which absorbs the sample that is present in the humidity, which contributes significantly to allow long-term sample storage by preventing growth of microorganisms and damage or degradation of the sample.

Sample Collection Protrusion

Figure 3A:
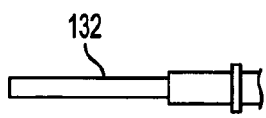
FIGS. 3A-3C show alternative embodiments of the sample collection protrusion.
Figure 3B:
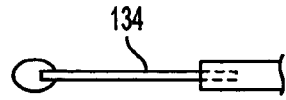
Figure 3C:
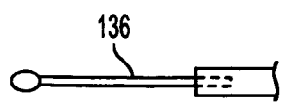
Figure 4:
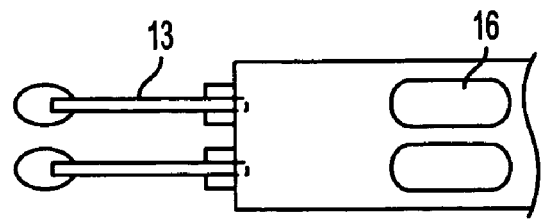
FIG. 4 shows alternative embodiment of the open and folded sample collection protrusion.
Figure 4:
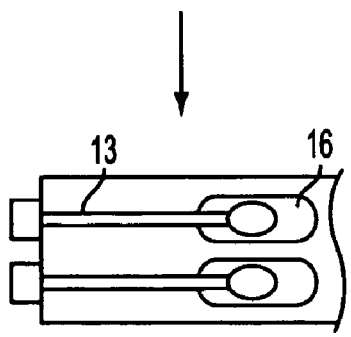

As exemplified in FIGS. 3A-3C and 4, the inventive sample collection device comprises a built-in sample collection protrusion or extension which has optionally connected at the tip of the protrusion a means for collecting samples that may bind to it, such as a wick in FIG. 3A (132), a swab in FIG. 3B (134), or a spoon in FIG. 3C (136). Any assortment of objects that may be used for the tip may be used including for example, a pick, which may be made of wood, metal, plastic or any other means to collect a sample. As shown in FIGS. 1A-1B, 2 and 4, the sample collection protrusion may be folded around a hinge (14), and may contact a sample reservoir pad (16) or space, which may optionally contain preservatives and inhibitors of degradative enzymes such as proteases or genetic material. In one embodiment, the sample collection protrusion may be folded into the device, which allows the wetted sample collection protrusion tip to contact sample reservoir pad and transfer the biological sample from the sample collection protrusion tip to the pad. The pad may be impregnated or coated with various inhibitors of microbiological growth and preservatives, including but not limited to DNase inhibitors, EDTA, buffers, sodium azide, sodium benzoate, procline, thimerosal and so on. The pad (16) may be made of any number of material is capable of storing the contents of the sample on the tip (12), and may include cloth, glue, felt, and so on. The sample collection protrusion may be removable to contact a sample reservoir pad. In another aspect of the invention, the sample collection protrusion may be used as a stand alone to store the sample at the protrusion tip.

The protrusion (13) may be made of any material at all, including but not limited to wood, plastic or metal such that the collection protrusion may be made of stiff or flexible material so long as the protrusion is capable of functioning as a sample gathering object. Further, it is recognized that the device may comprise at least one protrusion, preferably two or more.

Liquid Storage Area

As exemplified in FIGS. 1, 5A-5B, 6 and 7 the device comprises a liquid sample storage area (20), which is fit to hold any number of liquid samples, including but not limited to any biological sample, in particular those obtained from nature, including an individual's body fluid, cell line, tissue culture, or any other source, which may contain genetic material. As indicated, biological samples include body fluids, such as blood, semen, lymph, sera, plasma, urine, synovial fluid, spinal fluid, sputum, pus, sweat, as well as liquid samples from the environment such as plant extracts, pond water and so on.

The liquid storage area may be any shape so long as it is capable of holding its contents. For instance, the area may be a padded area to collect liquid biological samples, including whole blood, in which the liquid sample-collecting chamber may contain various chemical or natural preservatives or inhibitors. The preservatives and chemicals may be bound to the walls of the chamber or may be in contact with a pad placed in the chamber on which the liquid sample also may be deposited.

Figure 5A:
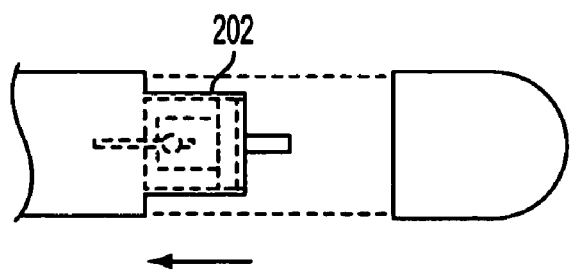
FIG. 5 shows alternative embodiment of the liquid storage area using a syringe.
Figure 5B:
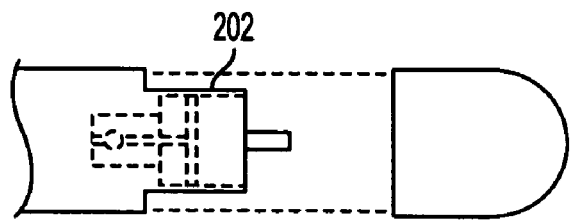
Figure 6:
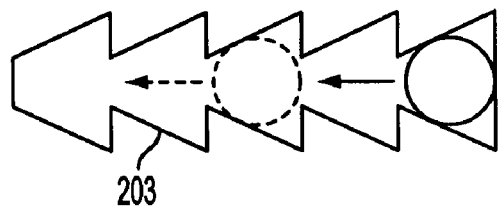
FIG. 6 shows alternative embodiment of the ridged piston of the liquid storage syringe for unidirectional movement.

In an alternative embodiment, as exemplified in FIGS. 5A-5B, the liquid storage chamber may be a syringe (202), or may be fitted with a syringe as a liquid sample collector, with an inlet through which the sample to be collected is transported into the syringe chamber, which may be especially useful for collecting liquid samples containing toxins. A piston that sealingly contacts the inner surface of the syringe is moved away from the inlet, thereby creating a vacuum, whereby the sample is sucked into the chamber of the syringe, or the sample may be partially or fully lodged in the inlet. Preferably, the piston has a unidirectional movement (203) as exemplified in FIG. 6 so that once the liquid sample is pulled into the storage chamber, the liquid is not pushed back out by virtue of the unidirectional movement of the piston. Such a piston may have at least one unidirectional ridge so that the piston locks as it passes through an opening and is caught by the edges surrounding the opening or another ridge located on the side of the opening. Alternatively, the inner or outer surface of the syringe barrel may have a ridge for the piston to clip or lock therewith.

Figure 7:
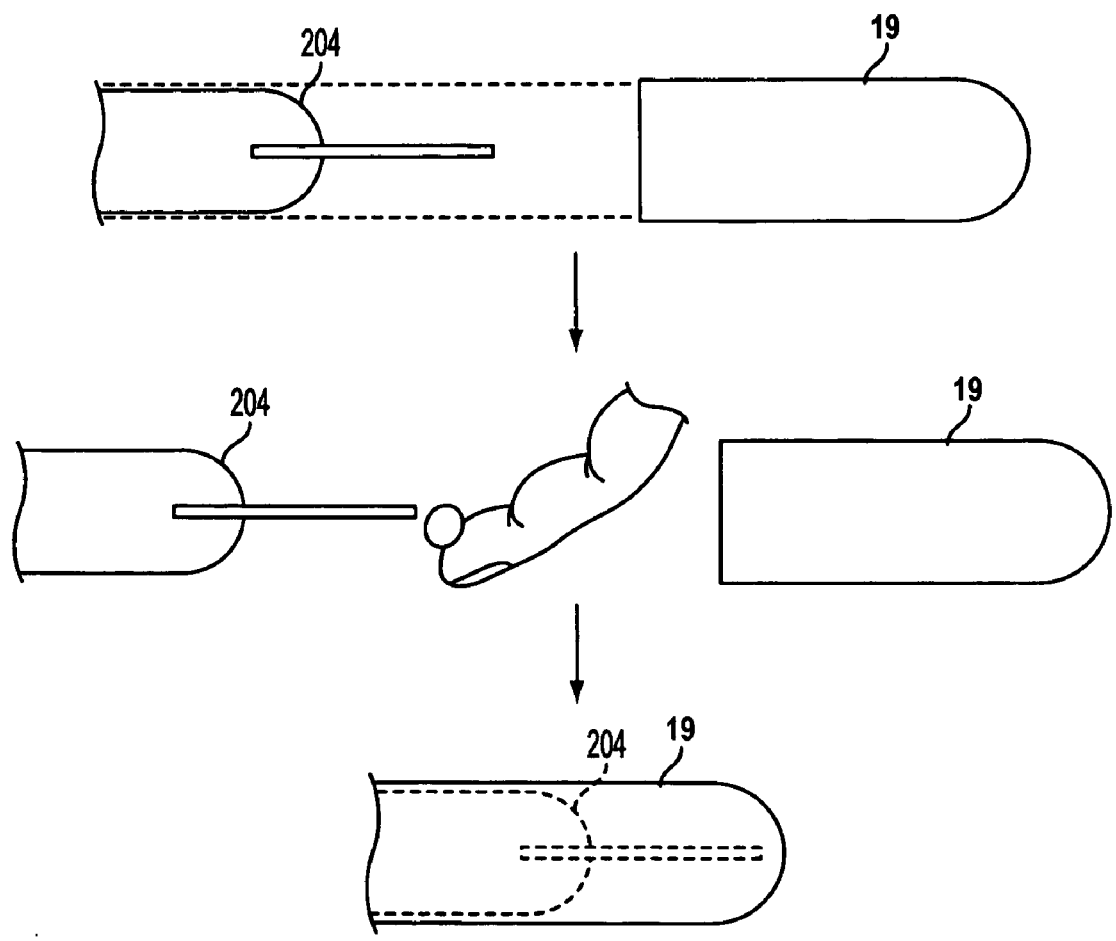
FIG. 7 shows alternative embodiment of the liquid storage chamber using a capillary tube.

In another embodiment, as exemplified in FIG. 7, the liquid storage chamber may be or may be fitted with a tube (204), such as a capillary tube, which may be used to draw liquid such as blood. After the liquid is drawn in, it may be capped. The cap may be coated with desiccant material and may be self-closing. The tube may be made of any material so long as it is able to draw in the sample through capillary action.

As can be seen, the various alternative embodiments of the liquid chamber may be combined with each other. For instance, capillary tube (204) or syringe liquid storage chamber (202) may contain preservative or chemical inhibitors for long term storage or optionally contacted with a pad (20) so that the liquid is deposited on the pad and optionally the liquid may be dried on the pad. The pad may be impregnated or coated with a preservative or chemical inhibitor for long-term storage.

Solid Specimen Storage Area

The solid specimen storage area (18) may be of any shape so long as the area, preferably in the shape of a chamber or container, can hold the solid object. Preferably, the chamber is covered with a lid. In an alternative embodiment, an adherent object or substance such as a clip or sticky substance such as glue may be placed on the area to securely adhere the solid specimen that is sought to be stored to the area or in the chamber. In another embodiment, a secured closing mechanism, such as a lock, is incorporated to prevent adulteration of the specimen or to prevent contamination. In yet another alternative embodiment, the solid specimen storage chamber has at least one aeration hole, preferably a plurality of holes, to maintain low humidity within the chamber.

Those skilled in the art will recognize, or be able to ascertain using no more than routine experimentation, many equivalents to the specific embodiments of the invention specifically described herein. Such equivalents are intended to be encompassed in the scope of the invention.

What is claimed is:

1. A device for collecting biological samples comprising:
   (i) at least one collection protrusion, which is attached to the body of the device, comprising at least one tip;
   (ii) at least one pad for contacting the tip, wherein the pad comprises chemical preservatives or enzyme inhibitors;
   (iii) at least one cap, which is coated with silica gel, a molecular sieve, or a desiccant and capable of sealingly enclosing the device; and
   (iv) at least one aeration hole.

2. The device according to claim 1, wherein the tip is a wick, spoon, pick, or swab.

3. The device according to claim 1, wherein the cap is connected to the device.

4. The device according to claim 1, wherein the cap is detached from the device.

5. The device according to claim 1, wherein the cap slidably encloses the device.

6. The device according to claim 1, wherein the device is made of plastic.

7. The device according to claim 1, wherein the chemical preservatives or enzyme inhibitors is selected from a group consisting of DNase inhibitors, EDTA, buffers, sodium azide, sodium benzoate, procline, and thimerosal.

8. The device according to claim 1, further comprising material with instructions on using the device.

9. The device according to claim 8, wherein the instructions are in written form.

10. The device according to claim 1, wherein at least one collection protrusion is foldable or removable.

11. The device according to claim 10, wherein the collection protrusion is foldable around a hinge.

12. A device for collecting biological samples comprising:
   (i) at least one collection protrusion comprising at least one tip;
   (ii) at least one pad for contacting the tip;
   (iii) a storage area for collecting liquid, wherein inside of the liquid storage area is coated with a chemical preservative or enzyme inhibitor; and
   (iv) at least one aeration hole, wherein the liquid storage area is fitted with a syringe.

13. The device according to claim 12, wherein the syringe is fitted with a unidirectional piston.

14. The device according to claim 12, wherein at least one collection protrusion is foldable or removable.

15. The device according to claim 12, comprising an area for gathering a solid sample.

16. The device according to claim 15, wherein the solid sample collection area comprises a lid.

17. A device for collecting biological samples comprising:
   (i) at least one collection protrusion comprising at least one tip;
   (ii) at least one pad for contacting the tip;
   (iii) a storage area for collecting liquid, wherein inside of the liquid storage area is coated with a chemical preservative or enzyme inhibitor; and
   (iv) at least one aeration hole, wherein the liquid storage area is fitted with capillary tube.

18. The device according to claim 17, wherein at least one collection protrusion is foldable or removable.

19. The device according to claim 17, comprising an area for gathering a solid sample.

20. The device according to claim 19, wherein the solid sample collection area comprises a lid.

* * * * *